(12) United States Patent
Otsubo et al.

(10) Patent No.: US 9,333,123 B2
(45) Date of Patent: May 10, 2016

(54) DISPOSABLE WEARING ARTICLES AND A SEAM WELDER USED TO FORM THE SAME

(75) Inventors: Toshifumi Otsubo, Kanonji (JP); Tatsuya Hashimoto, Kanonji (JP); Mariko Yamashita, Kanonji (JP); Taishi Nakamura, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 966 days.

(21) Appl. No.: 13/522,873

(22) PCT Filed: Feb. 10, 2011

(86) PCT No.: PCT/JP2011/000767
§ 371 (c)(1),
(2), (4) Date: Jul. 18, 2012

(87) PCT Pub. No.: WO2011/099297
PCT Pub. Date: Aug. 18, 2011

(65) Prior Publication Data
US 2012/0284904 A1    Nov. 15, 2012

(30) Foreign Application Priority Data
Feb. 10, 2010   (JP) ................... 2010-027855

(51) Int. Cl.
*B32B 37/00* (2006.01)
*A61F 13/496* (2006.01)
(Continued)

(52) U.S. Cl.
CPC ....... *A61F 13/4963* (2013.01); *A61F 13/15739* (2013.01); *A61F 13/15772* (2013.01);
(Continued)

(58) Field of Classification Search
CPC .. B29C 65/08; B29C 65/087; B29C 65/7885; B29C 65/7894; B29C 66/21; B29C 66/246; B29C 66/306; B29C 66/4312; A61F 13/4963; A61F 13/15739
USPC ................................ 156/73.1, 580.1, 580.2
See application file for complete search history.

(56) References Cited

U.S. PATENT DOCUMENTS 2,200,971 A    5/1940    Sonneborn et al.
4,632,667 A   12/1986    McDonald et al.
(Continued)

FOREIGN PATENT DOCUMENTS

DE        19804736 C1    2/1999
JP         2005205026    8/2005
(Continued)

OTHER PUBLICATIONS

International Search Report for PCT/JP2011/000767 mailed Apr. 19, 2011.
Written Opinion of the International Searching Authority mailed Apr. 19, 2011 in corresponding International Application No. PCT/JP2011/00767 filed Feb. 10, 2011.
(Continued)

*Primary Examiner* — James Sells
(74) *Attorney, Agent, or Firm* — Hauptman Ham, LLP (57) ABSTRACT

A wearing article includes front and rear side edges respectively joined by seam arrays extending in a longitudinal direction Y, a waist-opening, and a pair of leg-openings. The wearing article further includes an inner sheet, an outer sheet and a liquid-absorbent core sandwiched between these inner and outer sheets. The inner and outer sheets are formed of heat-sealable fibrous nonwoven fabrics containing thermoplastic synthetic resins. Each of the seam arrays of the diaper includes a plurality of seam-welded regions and a seam-nonwelded region left behind in the seam array. In the seam array, the seam-welded regions arranged so as to be aligned in longitudinal and transverse directions, each substantially shaped in a square, partially lack at a position differentiated for every one of specified patterns.

16 Claims, 9 Drawing Sheets

(51) Int. Cl.
| | |
|---|---|
| *B29C 65/08* | (2006.01) |
| *B29C 65/78* | (2006.01) |
| *B29C 65/00* | (2006.01) |
| *A61F 13/15* | (2006.01) |
| *B29L 31/48* | (2006.01) |
| *B29C 65/82* | (2006.01) |
| *B29C 37/00* | (2006.01) |

(52) U.S. Cl.
CPC .............. *B29C65/08* (2013.01); *B29C 65/087* (2013.01); *B29C 65/7885* (2013.01); *B29C 65/7894* (2013.01); *B29C 66/1122* (2013.01); *B29C 66/21* (2013.01); *B29C 66/246* (2013.01); *B29C 66/306* (2013.01); *B29C 66/431* (2013.01); *B29C 66/433* (2013.01); *B29C 66/4312* (2013.01); *B29C 66/7294* (2013.01); *B29C 66/73921* (2013.01); *B29C 66/81433* (2013.01); *B29C 66/81465* (2013.01); *B29C 66/8221* (2013.01); *B29C 66/83511* (2013.01); *B29C 66/83513* (2013.01); *B29C 66/83517* (2013.01); *B29C 65/8223* (2013.01); *B29C 66/83433* (2013.01); *B29C 66/876* (2013.01); *B29C 2037/80* (2013.01); *B29L 2031/4878* (2013.01)

(56) References Cited

U.S. PATENT DOCUMENTS

| | | | | |
|---|---|---|---|---|
| 4,713,132 | A * | 12/1987 | Abel | B29C 65/087 156/290 |
| 4,758,293 | A * | 7/1988 | Samida | B29C 65/08 156/308.4 |
| 5,660,679 | A * | 8/1997 | Rajala | B29C 66/431 156/580.1 |
| 6,145,562 | A * | 11/2000 | Voss | B29C 59/04 156/553 |
| 7,059,103 | B2 * | 6/2006 | Ninomiya | A61F 13/15739 156/308.2 |
| 7,383,865 | B2 * | 6/2008 | Umebayashi | A61F 13/15739 156/350 |
| 7,458,925 | B2 * | 12/2008 | Turvey | B29C 65/08 493/213 |
| 2002/0183183 | A1 | 12/2002 | Turvey | |

FOREIGN PATENT DOCUMENTS

| | | |
|---|---|---|
| JP | 2007030236 | 2/2007 |
| WO | 02078935 A1 | 10/2002 |

OTHER PUBLICATIONS

Supplementary European Search Report dated Aug. 12, 2014, corresponds to European patent application No. 11742046.3.

* cited by examiner

DISPOSABLE WEARING ARTICLES AND A SEAM WELDER USED TO FORM THE SAME

RELATED APPLICATIONS

The present application a national phase of PCT/JP2011/000767, filed Feb. 10, 2011 and is based on, and claims priority from, Japanese Application Number 2010-027855, filed Feb. 10, 2010.

TECHNICAL FIELD

The present disclosure relates to disposable wearing articles and more particularly to disposable wearing articles such as disposable diapers, disposable toilet-training pants, disposable incontinent pants or disposable menstruation pants. The present disclosure relates also to a seam welder used to form seam arrays in these wearing articles.

BACKGROUND ART

Conventionally, in disposable diapers comprising front and rear waist regions and a crotch region extending between these front and rear waist regions, it is known to join the front and rear waist regions together by seam arrays along the respective opposite side edges of the diapers. For example, PATENT DOCUMENT 1 (JP 2005-205026 A) discloses an apparatus by which the front and rear waist regions are put flat together and are nipped along respective opposite side edges by a nipper unit and then sonic-sealed together.

In such an apparatus, a web comprising continuously arranged disposable diapers is transported along an outer peripheral surface of a drum. Ultrasonic wave units projecting out from the inside of the drum cooperate with anvils coming in contact with the associated ultrasonic wave units from the outside of the drum to form seal arrays along which the side edges of the diaper are joined together. Specifically, respective pairs of the ultrasonic wave units and the anvils cooperate with each other to form the seal arrays and six (6) pairs of ultrasonic wave units and anvils are arranged along the outer periphery of the drum at regular intervals so that the seal arrays may be continuously formed. The surface of the anvil is formed with a plurality of protrusions so that the side edges of the diaper may be formed with the seal arrays in the same pattern as the pattern of the protrusions.

CITATION LIST

Patent Literature

[PATENT DOCUMENT 1] JP 2005-205026 A

SUMMARY OF INVENTION

Problem to be Solved by the Invention

In the apparatus disclosed in PATENT DOCUMENT 1 (JP 2005-205026 A), the protrusions of the anvil sometimes get chipped and/or abraded away and the ultrasonic wave unit itself sometimes oscillates abnormally. In such situation, weld strength of the seam arrays might be undesirably low. The weld strength of the seam arrays which is excessively low may sometimes cause the side edges of the diaper to be unintentionally peeled off. Usually, some diapers are extracted in a random manner from a plurality of the diapers immediately after they have been made and the weld strength of the seam arrays are inspected by actually pulling the side edges of the diapers to peel off the seam arrays. However, even if the diaper in which the weld strength of the seam arrays is unacceptably low, in order to identify the particular one in a plurality of anvils having formed this diaper with such defective seam arrays, all of the anvils must be inspected and a lot of trouble and time will be required.

Measure to Solve the Problem

The present invention includes a first aspect and a second aspect.

According to the first aspect of the present invention, there is provided a seam welder comprising an annular rotating body, a plurality of anvil units and a plurality of welding units wherein the anvil units come in contact with the welding units.

The first aspect of the present invention is characterized in that each of the anvil units comprises a nipper surface adapted to come in contact with the welding unit and a plurality of protrusions formed on the nipper surface wherein a pattern in which the protrusions are arranged is differentiated for every one of associated the anvil units.

According to the second aspect of the present invention, there is provided in a disposable wearing article having a pair of seam arrays comprising a given number of intermittently arranged seam-welded regions.

The second aspect of the present invention is characterized in that the seam arrays are formed by arranging the seam-welded regions in a plurality of patterns differentiated for every one of a plurality of disposable wearing articles so that these disposable wearing articles may be identified from one another.

DETAILED DESCRIPTION OF THE PREFERRED EMBODIMENTS

Referring to FIGS. 1 to 4, the diaper 1 has the imaginary longitudinal center line P-P bisecting a width dimension, in a transverse direction Y, and the imaginary transverse center line Q-Q bisecting a length dimension, in a longitudinal direction Y, wherein the diaper 1 is substantially symmetric about the imaginary longitudinal center line P-P. Of the portions paired in symmetric relationship about the imaginary longitudinal center line P-P, only one of them will be designated by reference numeral and the other will be sometimes not designated by reference numeral.

Figure 1:
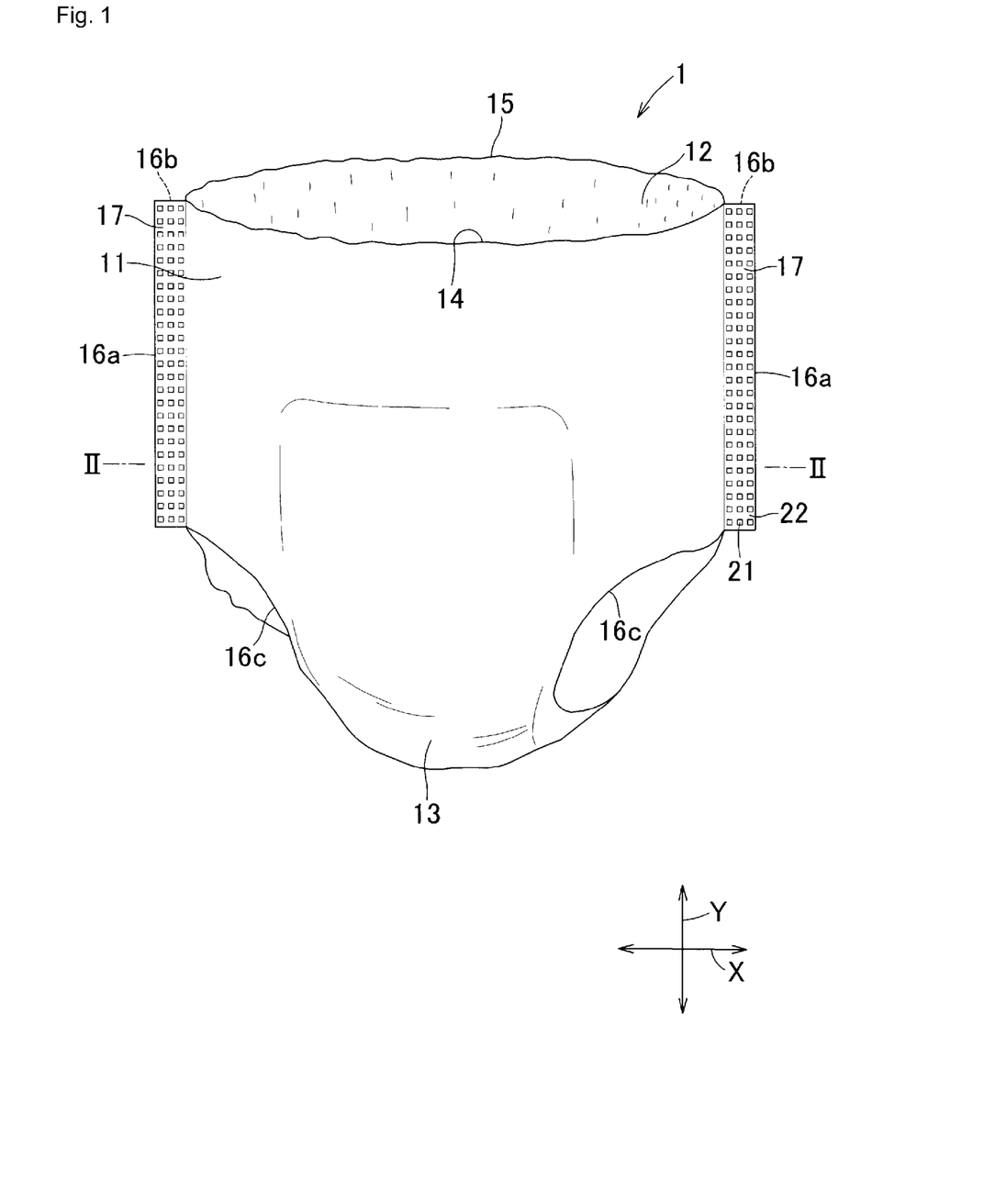
FIG. 1 is a perspective view of a disposable diaper as one example of disposable wearing articles.
Figure 2:
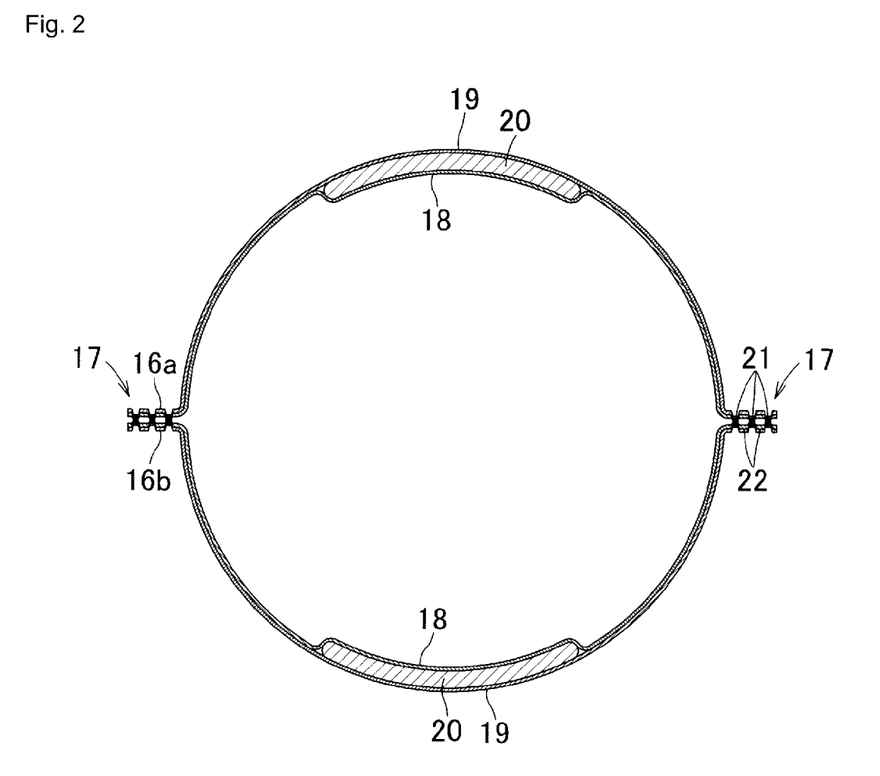
FIG. 2 is a sectional view taken along the line II-II in FIG. 1.
Figure 3:
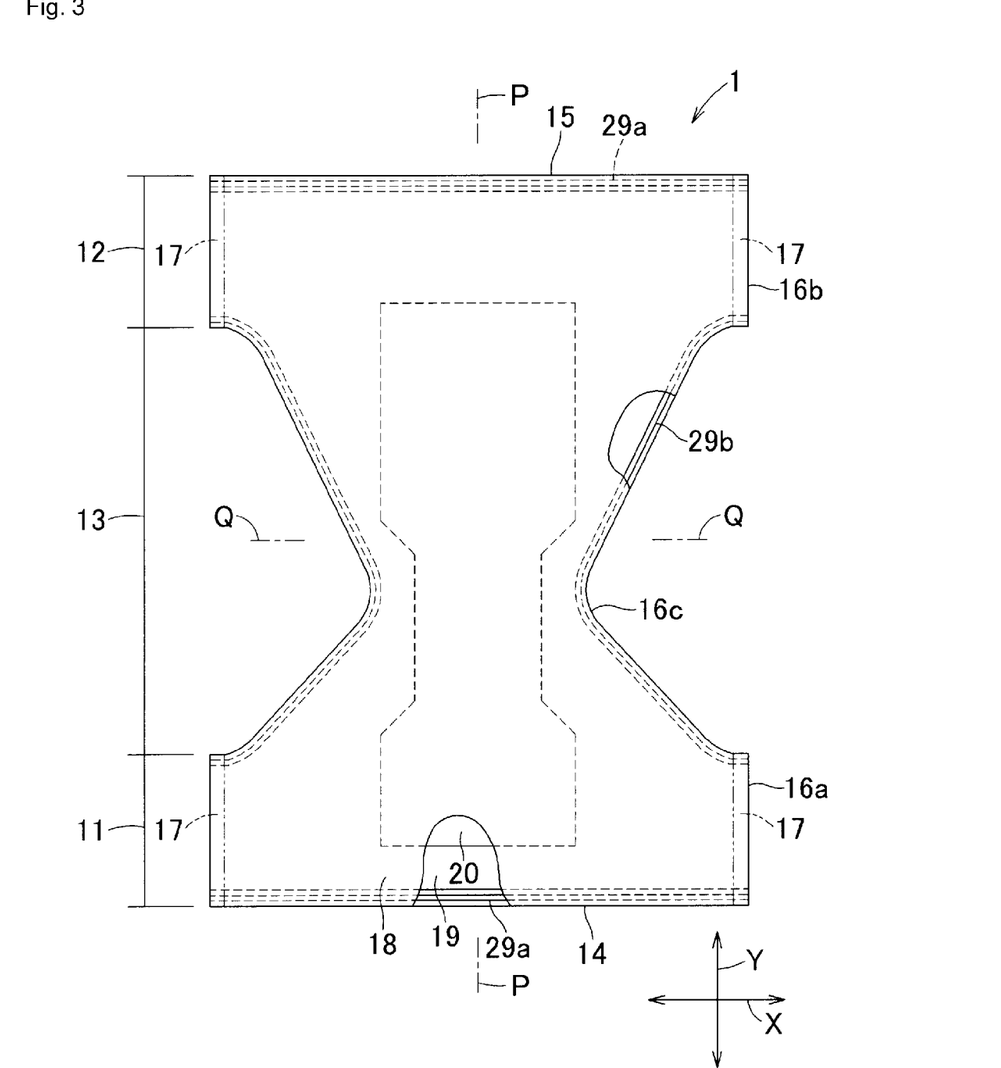
FIG. 3 is a partially cutaway developed plan view of the diaper.

The diaper 1 comprises a skin-facing side, a garment-facing side, a front waist region 11, a rear waist region 12, a crotch region 13 extending between the front and rear waist regions 11, 12, front and rear ends 14, 15 opposed to each other about the imaginary transverse center line Q-Q and extending in the transverse direction X and side edges 16 opposed about the imaginary longitudinal center line P-P. The side edges 16 include front side edges 16a lying in the front waist region 11, rear side edges 16b lying in the rear waist region 12 and crotch side edges 16c lying in the crotch region 13.

While the front and rear side edges 16a, 16b extend substantially in parallel to the imaginary longitudinal center line P-P, the crotch side edges 16c are concavely curved to be put in close contact with the wearer's inguinal regions to provide a good fit. The front side edges 16a and the rear side edges 16b are joined together by seam arrays 17 extending in the longitudinal direction Y and thereupon a waist-opening and a pair of leg-openings are formed.

The diaper 1 comprises an inner sheet 18 defining the side facing the wearer's body, an outer sheet 19 facing the wearer's garment and a liquid-absorbent core 20 sandwiched between these inner and outer sheets 18, 19. These inner and outer sheets 18, 19 are intermittently bonded to each other by bonding means such as hot melt adhesives and the core 20 and the inner and outer sheets 18, 19 are also intermittently bonded one to another by bonding means such as hot melt adhesives. Between the inner and outer sheets 18, 19, two or more elastic members 29a, 29b are contractibly attached under tension and in parallel to the front and rear ends 14, 15 and the crotch side edges 16c so that the diaper 1 may be put in close contact with the wearer's body.

The inner and outer sheets 18, 19 are formed of heat-weldable fibrous nonwoven fabrics containing thermoplastic synthetic resins. As heat-weldable fibers, for example, spun bonded fibrous nonwoven fabrics containing polypropylene fibers or polyethylene fibers may be used. The inner sheet 18 is preferably liquid-pervious and the outer sheet 19 is preferably liquid-impervious.

The core 20 lies at least in the crotch region 13 and further extends in the longitudinal direction Y into the front and rear waist regions 11, 12. The core 20 has its width dimension, in the transverse direction X, gradually reduced in the crotch region 13 to be nipped-in in the imaginary transverse direction Q-Q. Such core 20 may be formed by wrapping a core material including a mixture of, for example, fluff pulp fibers and super-absorbent polymer particles with a liquid-dispersant sheet (not shown).

Figure 4:
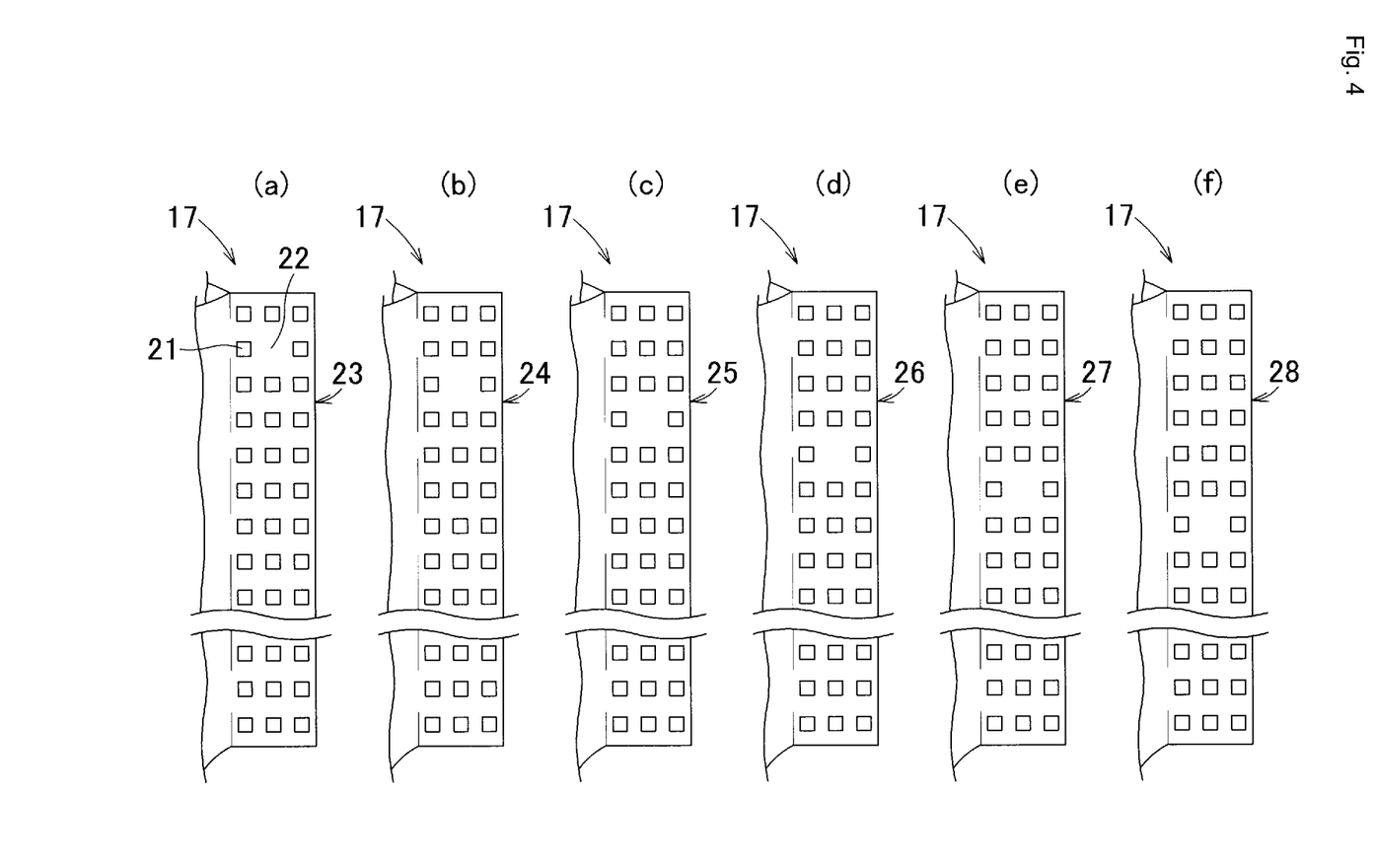
FIG. 4 is a diagram illustrating a pattern of seams along side edges of the diaper.

FIG. 4 exemplarily illustrates patterns of the seam arrays 17 in the diapers belonging to a specified groups of the diapers (wearing articles). It should be appreciated that, in FIG. 4, only one half of each seam array pair is illustrated for convenience of illustration. The seam arrays 17 of each diaper 1 comprise a plurality of seam-welded regions 21 and seam-nonwelded regions left behind in the respective seam arrays 17. The plural seam-welded regions 21 each provided in a square shape of about 1 mm on a side are formed and a plurality of such squares are arranged to be aligned in the longitudinal direction as well as in the transverse direction. In each of these seam-welded regions, respective component fibers of the inner and outer sheets 18, 19 are partially heat-sealed and joined together. The seam-nonwelded regions left behind in the respective seam arrays 17 serve to alleviate bonding force and stiffness of the seam arrays 17 and thereby to prevent the seam arrays 17 from creating a feeling of discomfort to the wearer.

Each of the diapers 1 of the construction as has been described hereinabove is made with respect to each size and a plurality of diapers of the same size is put in a package. According to the present embodiment, all of the diapers 1 put in one package respectively have the seam arrays 17 arranged in different patterns.

The substantially square-shaped seam-welded regions 21 arranged to be aligned in the longitudinal direction Y as well as in the transverse direction X are omitted in different regions depending on the respective pattern. Specifically, the second seam-welded region 21 from the top on the second (central) column is omitted in a first pattern 23 of FIG. 4(a), the third from top seam-welded region 21 to lie on the second column is omitted in a second pattern 24 of FIG. 4(b), the fourth from top seam-welded region 21 to lie on the second column is omitted in a third pattern 25 of FIG. 4(c), the fifth from top seam-welded region 21 to lie on the second column is omitted in a fourth pattern 26 of FIG. 4(d), the sixth from top seam-welded region 21 to lie on the second column is omitted in a fifth pattern 27 of FIG. 4(e) and the seventh from top seam-welded region 21 to lie on the second column is omitted in a sixth pattern 28 of FIG. 4(f).

Figure 5:
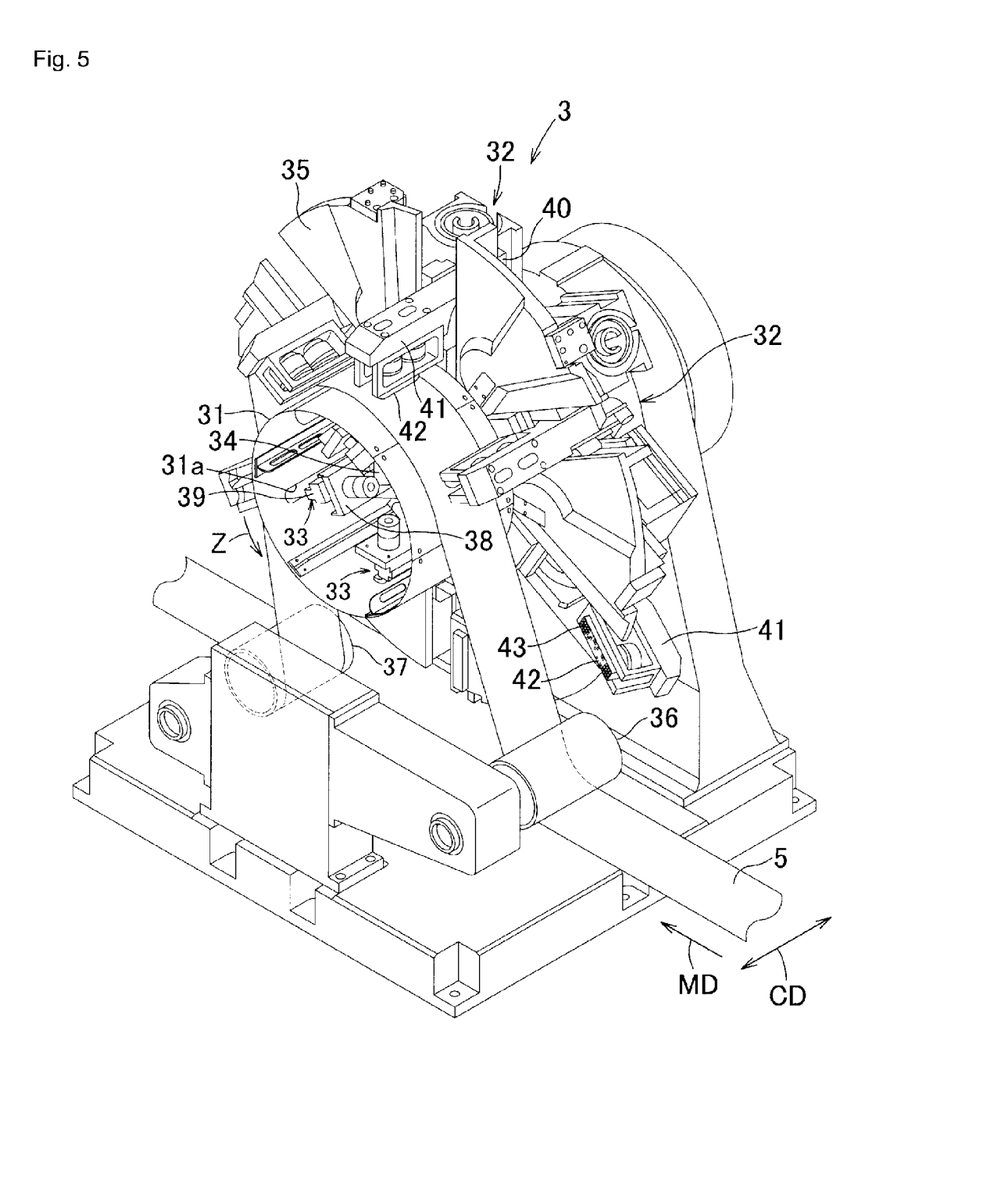
FIG. 5 is a perspective view of a seam welder.
Figure 6:
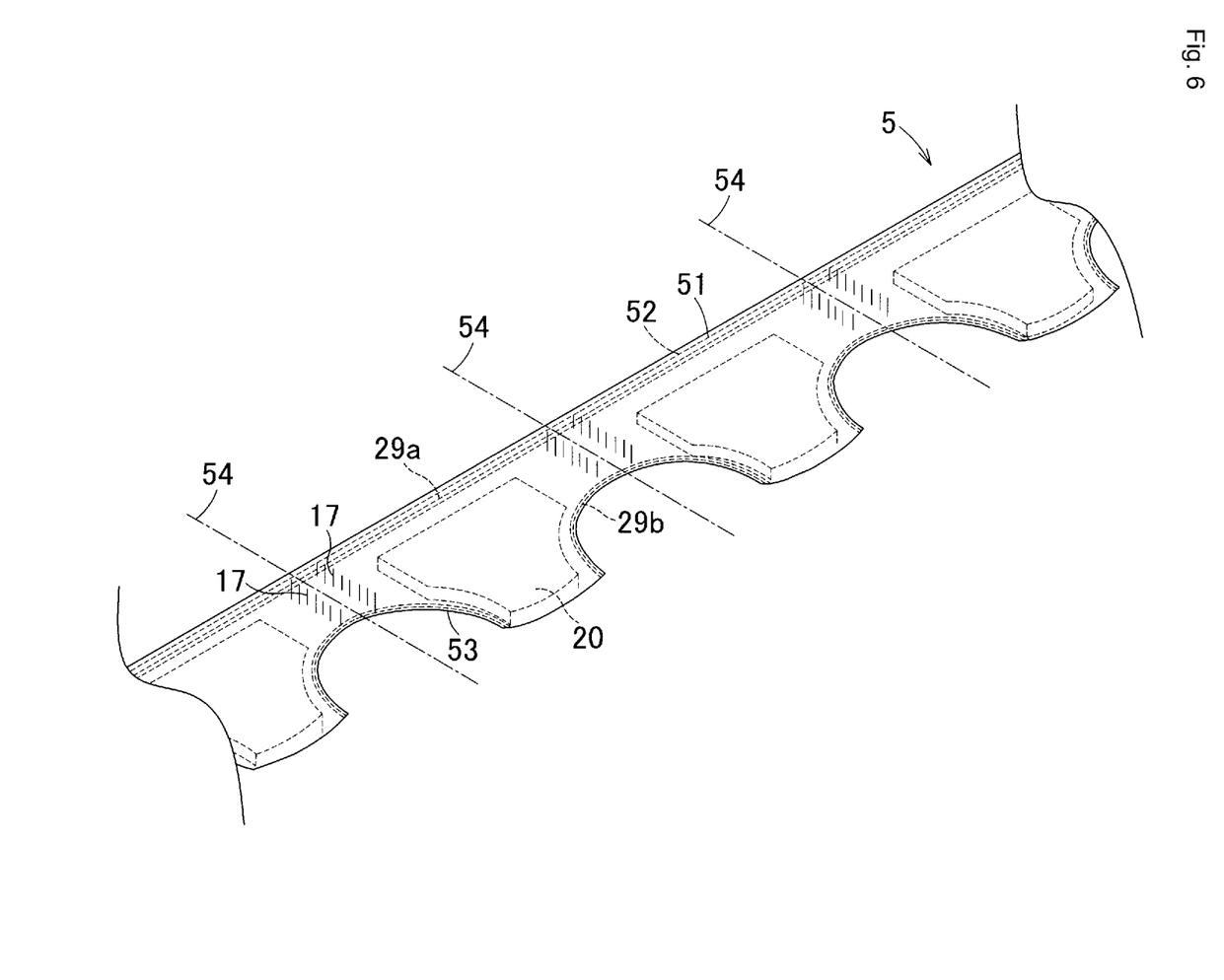
FIG. 6 is a schematic perspective view of a web.

FIG. 5 is a perspective view of a seam welder used to the form the diaper 1 with the seam arrays as have been described above and FIG. 6 is a diagram illustrating web 5 being fed to the seam welder 3. The web 5 continuously extending in a machine direction MD is cut off along imaginary cutting lines 54 to obtain the individual diapers 1. In the web 5 fed in this manner, both side edges 51, 52 corresponding to the front and rear ends 14, 15 of the diaper 1 overlap each other, i.e., the section corresponding to the front waist regions and the rear waist regions are put flat together. Such web 5 is formed with the seam arrays 17 by the seam welder 3. The web 5 is formed with openings 53 respectively having peripheral edges corresponding to the crotch side edges 16c. Between each pair of the adjacent openings 53, the core 20 is attached so that the web 5 may be formed with the cores 20 intermittently in the machine direction MD. The seam array 17 is formed between each pair of the adjacent opening 53 and the core 20 and the imaginary cutting line 54 lies between each pair of the adjacent seam arrays 17.

The seam welder 3 comprises an annular rotating body 31 having an outer peripheral surface along which the fibrous web 5 is transported, a plurality of anvil units 32 lying outside the rotating body 31 and a plurality of ultrasonic wave units 33 lying inside the rotating body 31 to be opposed to the associated anvil units 32. According to the present embodiment, both the anvil units 32 and the ultrasonic wave units 33 respectively lie at six (6) positions defined at regular intervals.

Both the anvil units 32 and the ultrasonic wave units 33 are mounted on support means 34, 35, respectively, and controlled (not shown) to revolve in the direction of the arrow Z in synchronism with rotation of the rotating body 31 in a direction of the arrow Z. The rotating body 31 and the support means 34, 35 are respectively driven by a drive source such as an electric motor (not shown).

The web 5 is transported by a guide roller 36 located on upstream side of the rotating body 31 to the rotating body 31, then transported along the outer peripheral surface of the rotating body 31 in the machine direction MD and finally transported by another guide roller 37 located on downstream side of the rotating body 31 out from the seam welder 3.

Each of the ultrasonic wave units 33 has an ultrasonic wave generator 38 and an oscillating surface 39 facing the associated anvil unit 32. The oscillating surface 39 projects out through a through-hole 31a formed in the rotating body 31 from inside the rotating body 31 and emits ultrasonic waves generated by the ultrasonic wave generator 38 toward the associated anvil unit 32.

The anvil unit 32 includes a fixed arm 40 fixed to the support means 35 and a rocking arm 41 linked to the fixed arm 40 so that the rocking arm 41 may revolve by an angle of 90° relative to the fixed arm 40 and come in contact with the oscillating surface 39 of the ultrasonic wave unit 33. The rocking arm 41 revolves relative to the fixed arm 40 under control of a cam mechanism (not shown). A distal end of the rocking arm 41 is provided with a nipper surface 42 opposed to the oscillating surface 39 so that the web 5 may be held between the oscillating surface 39 and the nipper surface 42. The nipper surface 42 is formed with a plurality of protrusions 43 adapted to be pressed against the oscillating surface 39 and thereby to form the web 5 with seam-welded regions corresponding to the protrusions 43.

Plural pairs of the anvil unit 32 and the ultrasonic wave unit 33 cooperating to form the seam-welded regions are arranged along the peripheral surface of the rotating body 31 at regular intervals so that the web 5 may be successively formed with the seam array 17. As will be apparent from FIG. 6, the seam array 17 can be formed between each pair of the adjacent core 20 and core 20 arranged intermittently in the machine direction MD and therefore the respective pairs of the anvil unit 32 and the ultrasonic wave unit 33 may be located depending on the core 20 to core 20 distance.

Figure 7:
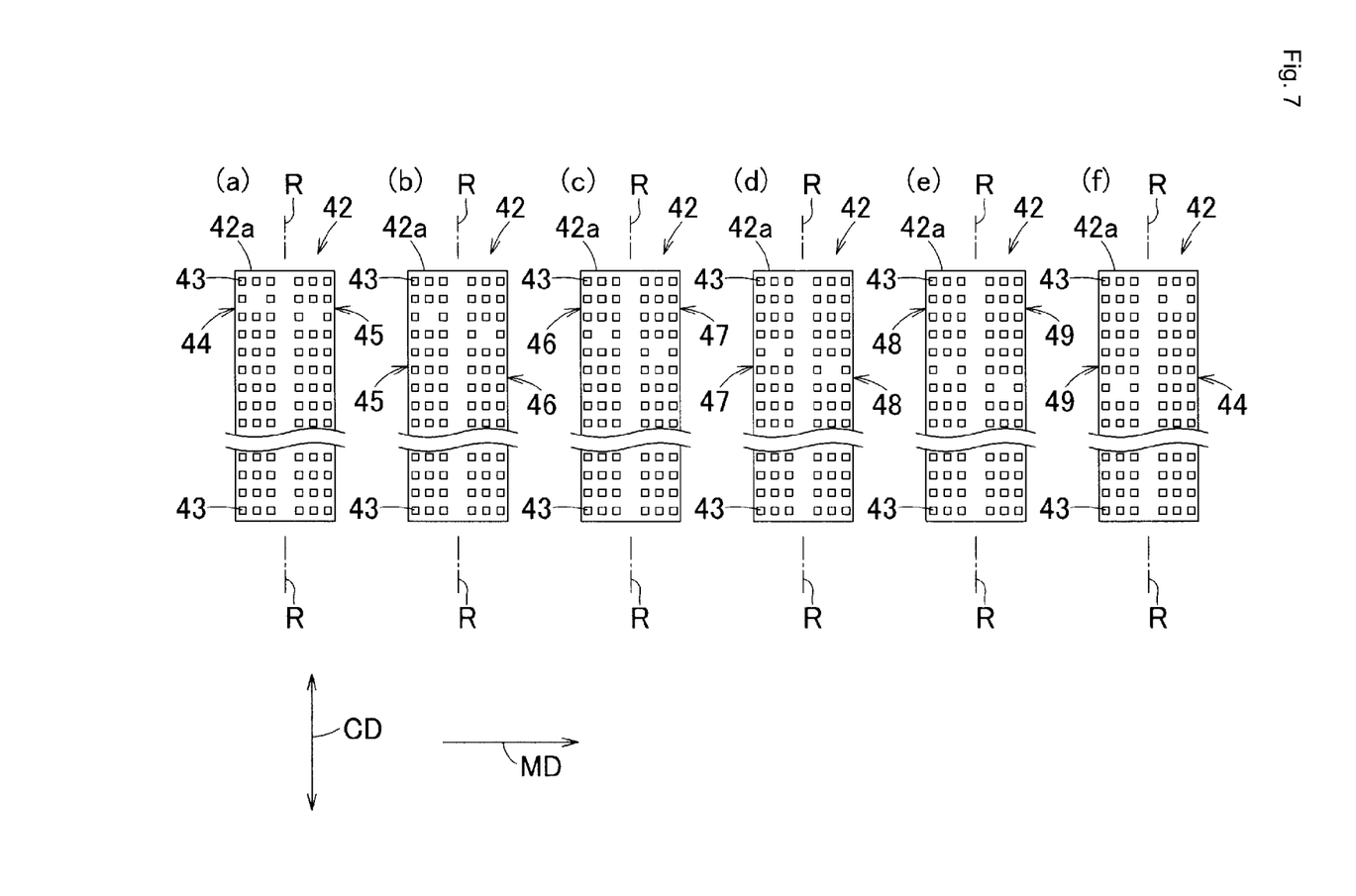
FIG. 7 is a diagram illustrating a pattern of protrusions on a nipping surface.

FIG. 7 is a diagram illustrating the protrusions 43 arranged on the nipper surfaces 42. The protrusions 43 each formed as a square of about 1 mm on a side are provided and a plurality of such squares are arranged to be aligned in the machine direction MD as well as in the cross direction CD at a regular intervals in a range of about 0.5 to 2.0 mm. The nipper surface 42 has arrays of the protrusions 43 arranged in different patterns between right half and left half of the nipper surface 42 about the imaginary longitudinal center line R-R bisecting a length dimension of the nipper surface 42 in the cross direction.

FIG. 7(a) through FIG. 7(f) illustrate patterns of the protrusions 43 on the respective nipper surfaces 42 adjacently arranged from the upstream toward the downstream in the machine direction MD. On the nipper surface 42 illustrated in FIG. 7(a), one of the protrusions 43 to lie in the second row in descending order from the end 42a of the nipper surface 42 lacks (is omitted) according to a first pattern 44 on the left half about the imaginary longitudinal center line R-R as viewed in FIG. 7 and one of the protrusions 43 to lie in the third row lacks according to a second pattern 45 on the right half. On the nipper surface 42 illustrated in FIG. 7(b), one of the protrusions 43 to lie in the third row lacks according to the same pattern as the second pattern 45 in FIG. 7(a) on the left half about the imaginary longitudinal center line R-R and one of the protrusions 43 to lie in the fourth row lacks according to a third pattern 46 on the right half.

On the nipper surface 42 illustrated in FIG. 7(c), one of the protrusions 43 to lie in the fourth row lacks according to the same pattern as the third pattern 46 in FIG. 7(b) on the left half about the imaginary longitudinal center line R-R and one of the protrusions 43 to lie in the fifth row lacks according to a fourth pattern 47 on the right half. On the nipper surface 42 illustrated in FIG. 7(d), one of the protrusions 43 to lie in the fifth row lacks according to the same pattern as the fourth pattern 46 in FIG. 7(c) on the left half about the imaginary longitudinal center line R-R and one of the protrusions 43 to lie in the sixth row lacks according to a fifth pattern 48 on the right half. On the nipper surface 42 illustrated in FIG. 7(e), one of the protrusions 43 to lie in the sixth row lacks according to the same pattern as the fifth pattern 48 in FIG. 7(d) on the left half about the imaginary longitudinal center line R-R and one of the protrusions 43 to lie in the seventh row lacks according to a sixth pattern 49 on the right half. On the nipper surface 42 illustrated in FIG. 7(f), one of the protrusions 43 to lie in the seventh row lacks according to the same pattern as the sixth pattern 49 in FIG. 7(d) on the left half about the imaginary longitudinal center line R-R and one of the protrusions 43 to lie in the second row lacks according to the same pattern as the first pattern 44 on the right half.

The web 5 formed with the seam array 17 corresponding to a plurality of the protrusions 43 as have been described just above may be cut off along an imaginary cutting line 54 coinciding with the imaginary longitudinal center line R-R to obtain the individual diapers 1. By shaping and arranging the protrusions 43 as has been described above, the seam arrays 17 corresponding to the patterns of the protrusions 43 can be formed along the opposite side edges of the respective diapers 1 as the diapers 1 are successively processed through the seam welder.

In the course of processing the diapers 1 through the seam welder 3, the diapers 1 having the seam arrays 17 according to the first through sixth patterns corresponding to the first through sixth patterns 44 of the protrusions 43 are obtained. Even when one diaper 1 is randomly extracted from a plurality of the produced diapers 1, it is possible to identify the particular anvil unit 32 of which the nipper surface 42 has formed the seam arrays 17 of this diaper 1 merely by checking the patterns of these seam arrays 17. Consequentially, when the weld strength of the seam arrays 17 is unacceptably low and it is deduced that any one or more of the anvil units 32 and/or the ultrasonic wave units 33 might be defective, the anvil unit(s) 32 and/or the ultrasonic wave unit(s) 33 can be easily identified. For this identification, it is unnecessary to inspect all the anvil units 32 and/or the ultrasonic wave units 33 and, in consequence, repair and/or exchange of these units can be significantly simplified.

While each of the seam-welded region 21 has a rectangular shape according to the present embodiment, the invention is not limited to this and, for example, the seam-welded regions 21 may comprise triangular regions which are uniform in shape as well as in size or a combination of different shaped regions, for example, a combination of rectangular regions and triangular regions.

While the ultrasonic welding method has been exemplarily described as the method to form the seam-welded regions 21, pressure- or heat-welding methods may be employed for this purpose. In this case also, the anvils each having the protrusions adapted to form the seam-welded regions 21 and the patterns of the protrusions may be varied to facilitate operations such as inspecting and repairing. It should be noted here that, in the case of the pressure-welding, it is not essential for the sheet prepared to be formed with the seam-welded regions 21 to contain thermoplastic synthetic resin.

Figure 8:
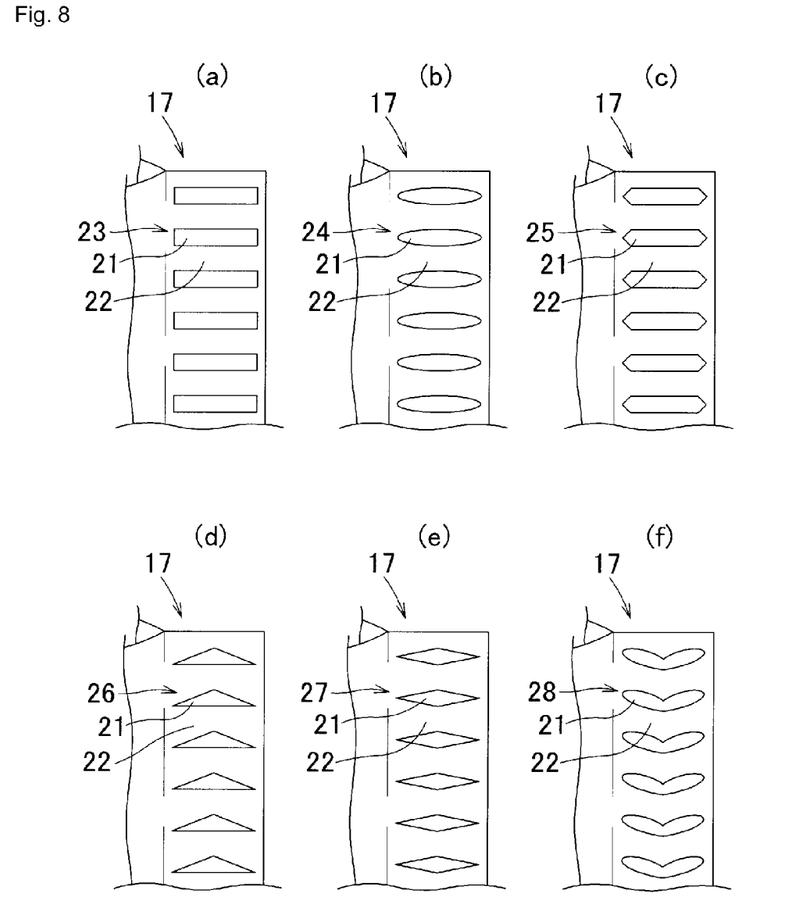
FIG. 8 is a diagram illustrating another pattern of seams along side edges of the diaper.
Figure 9:
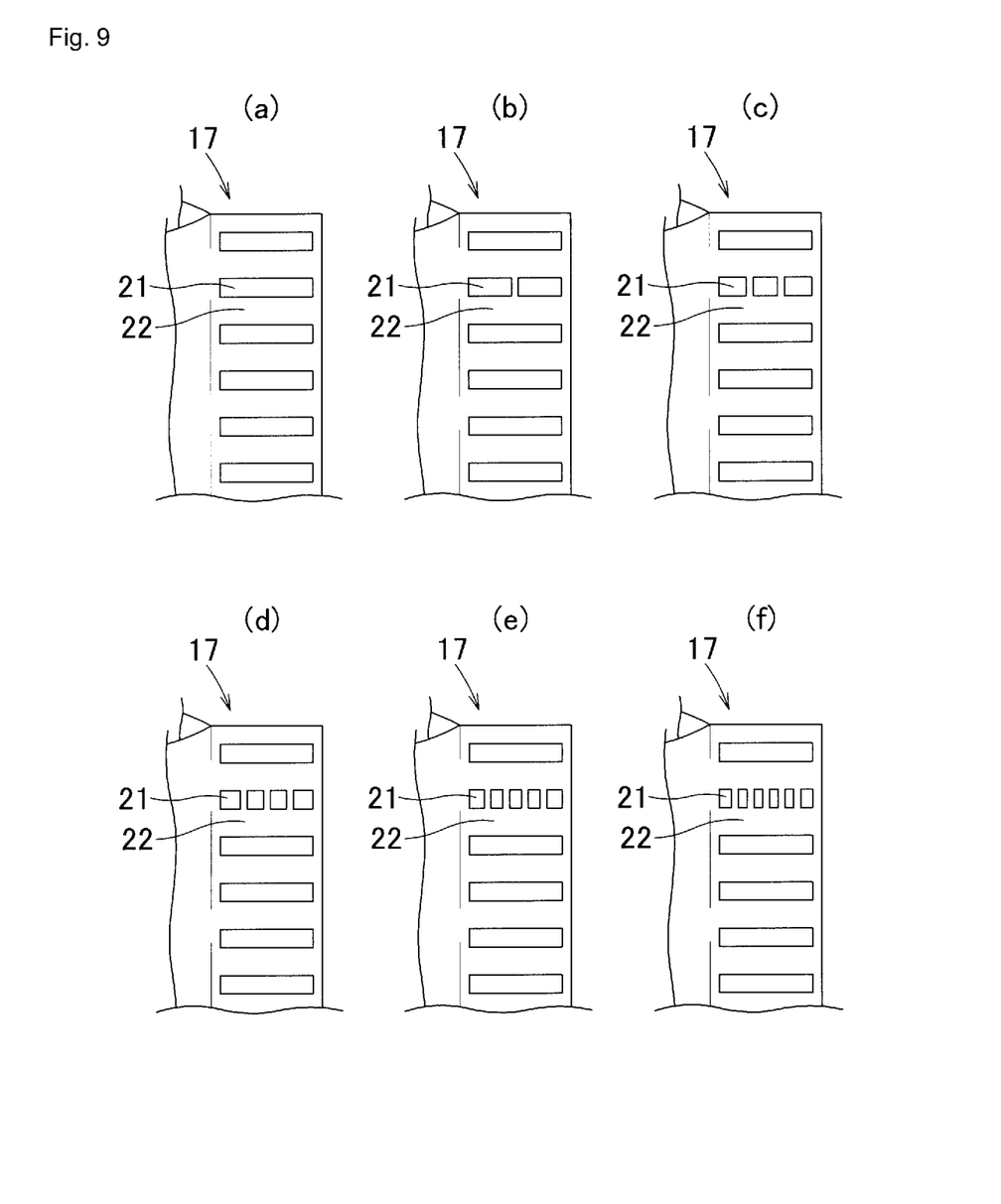
FIG. 9 is a diagram illustrating still another pattern of seams along side edges of the diaper.

FIGS. 8 and 9 are diagrams illustrating further alternative patterns of the seam array 17 wherein only one half of the paired seam arrays 17 for every diaper 1 are illustrated for convenience of illustration. Referring to FIG. 8, one group of wearing articles, the seam-welded regions 17 may have rectangular shapes as the first pattern 23, oval shapes as the second pattern 24, hexagonal shapes as the third pattern 25, triangular shapes as the fourth pattern 26, rhombic shapes as the fifth pattern 27 and heart shapes as the sixth pattern 28. Alternatively, the number of the seam-welded regions 21 in the respective second rows in the descending order may be varied. Whatever the case may be, the respective anvil units may be formed with the protrusions according to different patterns to obtain a group of the diapers provided with the seam-welded regions according to a plurality of patterns.

When a plurality of the diapers 1 made by the method as has been described above is put into a package and sold, a plurality of the diapers 1 having the seam-welded regions according to a plurality of patterns are present in one and same package. The pattern of the seam-welded regions 17 changes for every diaper 1 and the user may interestedly select a fresh diaper 1 from those in one and same package when the used diaper 1 is exchanged with the fresh one.

The pattern of the seam-welded regions 21 is preferably selected in consideration of the weld strength of the seam array 17 because the weld strength depends on the pattern. For example, when it is tried to form the partially lacking seam-welded regions 21, a central region of the seam array 17 in the longitudinal direction Y and the transverse direction X may be selected as the lacking region to prevent the weld strength from deteriorating. The area of each seam-welded region 21 may be reduced to assure the pattern to be varied without apprehension that a partial lack of the seam-welded region 21 might affect the weld strength of the seam array 17 as a whole. The partial lack of the seam-welded regions 21 is advantageous also in view of the effect such that the weld strength can be partially adjusted. For example, the front and rear waist regions include portions of which the weld strength might otherwise become excessively increase due to the number of sheets required for article's construction. By partially adjusting the weld strength, this problem can be effectively overcome.

Materials for the respective component members of the diaper 1 are not limited to those described in this specification and various other materials widely used in the related technical field may be selectively used.

As used herein, the term "a plurality of disposable wearing articles" refers to, for example, in the case of disposable diaper, various types of disposable diapers to be identified depending on size, intended purpose, age in month, specifically whether the diaper is for adult, for infant, for usual defecation, for daytime wearing, for nighttime wearing, for toilet training, and configuration such as appearance design and internal construction, performance, price, trademark or other factors.

The first aspects of the present invention described above may be arranged in at least the following items:

(i) A seam welder comprising an annular rotating body, a plurality of welding units and a plurality of anvil units arranged to come in contact with the welding units, wherein:

each of the anvil units comprises a nipper surface adapted to come in contact with a respective one of the welding units, and a plurality of protrusions is formed on each of the nipper surfaces wherein a pattern in which the protrusions are arranged is differentiated for every one of the anvil units.

The second aspects of the present invention described above may be arranged in at least following items:

(xi) A plurality of disposable wearing articles each having a pair of seam arrays comprising a plurality of intermittently arranged seam-welded regions, wherein:

the seam arrays are formed by arranging the seam-welded regions in a plurality of patterns differentiated for every one of the disposable wearing article so that these disposable wearing articles are identified from one to another.

The plurality of disposable wearing articles are preferably structurally identical to one another.

The first and second aspects of the present invention described in the above items (i) and (xi) may provide one or more of the following advantageous effects:

(a) The respective seam arrays have a plurality of patterns defined by the seam-welded regions and each of the patterns is differentiated for every one belonging to the disposable wearing articles so that these disposable wearing articles may be identified on the patterns. In the seam welder, a plurality of anvils adapted to form the patterns may be used to facilitate the anvil corresponding to the particular pattern to be identified. In this way, should any one of the anvils become defective, inspection can be easily carried out.

Additionally, one or more of the following embodiments are provided in accordance with further aspects:

(ii) The welding units are ultrasonic wave units, which are arranged to emit ultrasonic waves to the anvil units when the anvil units and the ultrasonic wave units are brought into contact with one another.

(iii) The welding units are pressure or heat welding units.

(iv) Each of the anvil units comprises a fixed arm attached to a support means adapted to be rotated in the same direction as the direction in which the rotating body rotates and a rocking arm adapted to rock relatively to the fixed arm and wherein the anvil units are arranged outside the rotating body.

(v) Each of the nipper surfaces features two different arrays of protrusions each of which comprises a different pattern of protrusions to the other.

(vi) The two different arrays of protrusions are arranged one either side of a longitudinal centerline of the nipper surface, wherein the longitudinal centerline extends perpendicular to the transverse direction.

(vii) Adjacent arrays of adjacent anvil units are identical but non adjacent arrays of the adjacent anvil units are different.

(viii) Each of the patterns in which the protrusions are arranged comprises a plurality of regularly spaced protrusions, wherein the patterns are differentiated from one another by the omission of one or more different protrusions from each of the patterns.

(ix) Each of the patterns comprises protrusions having a dimension of about 1 mm and being spaced from one another in both the longitudinal and transverse directions by about 0.5 to 2 mm.

(x) Each of the patterns comprises columns of protrusions that are aligned in the longitudinal direction and rows of protrusions that are aligned in the transverse direction and wherein, the select protrusions are omitted from a central portion of the pattern.

(xii) Each of the seam arrays comprises the seam-welded regions and seam-nonwelded regions left behind in the seam array; and the patterns are defined by varying locations of the seam-welded regions and the seam-nonwelded region for every one of the disposable wearing articles.

(xiii) The seam-welded regions are formed to be aligned in at least one of a longitudinal direction and a transverse direction and the patterns are defined by a position at which at least one of the seam-welded regions is omitted.

(xiv) The patterns are defined by varying the shape of the seam-welded regions for every one of the disposable wearing articles.

(xv) A plurality of the wearing articles each having a plurality of the seam arrays arranged in the patterns and differentiated for every one of the wearing articles is put in one and same package.

(xvi) A package of the wearing articles each having a plurality of the seam arrays arranged in the patterns and differentiated for every one of the wearing articles.

(xvii) A method of manufacturing wearing articles comprising: arranging a plurality of anvil units along a machine direction; arranging a plurality of welding units each corresponding to one of the anvil units to define therebetween a nip, wherein each of the anvil units comprises a nipper surface adapted to define the nip with the respective ultrasonic wave unit, and a plurality of protrusions formed on the nipper surface wherein a pattern in which the protrusions are arranged is unique for the anvil unit and different from those of the other anvil units; feeding a web with at least two layers placed one on top another in the machine direction through the nips and welding the layers together in the nips in different seam arrays having different the patterns.

According to the embodiments in the above (ii) to (x) and (xii) to (xvii), the features of which may be taken in isolation or in combination with one another, the advantageous effect(s) set forth at (a) is/are better ensured. Further advantageous effects of the respective embodiments may be obtained as discussed in the respective related descriptions.

As used herein, the terms "first", "second", "third" and "fourth" etc. are use merely for distinguishing between similar elements.

The invention claimed is:

1. A seam welder comprising an annular rotating body, a plurality of welding units and a plurality of anvil units arranged to come in contact with said welding units, wherein:
each of said anvil units comprises a nipper surface adapted to come in contact with a respective one of said welding units, and a plurality of protrusions is formed on each of said nipper surfaces wherein a pattern in which said protrusions are arranged is differentiated for every one of said anvil units.

2. The seam welder defined by claim 1, wherein said welding units are ultrasonic wave units, which are configured to emit ultrasonic waves to said anvil units when said anvil units and said ultrasonic wave units are brought into contact with one another.

3. The seam welder defined by claim 1, wherein said welding units are pressure or heat welding units.

4. The seam welder defined by claim 1, wherein
each of said anvil units comprises
a fixed arm attached to a support rotatable in a same direction as a direction in which said rotating body rotates, and
a rocking arm adapted to rock relatively to said fixed arm, and
said anvil units are arranged circumferentially outside said rotating body.

5. The seam welder defined by claim 1, wherein
each of said nipper surfaces has two different arrays of protrusions, and
each of the arrays comprises a different pattern of protrusions from the other.

6. The seam welder defined by claim 5, wherein
said two different arrays of protrusions are arranged on either side of a longitudinal centerline of said nipper surface, and
said longitudinal centerline extends perpendicular to a transverse direction of the nipper surface.

7. The seam welder defined by claim 6, wherein
the patterns of the protrusions in adjacent arrays of adjacent anvil units are identical, and
the patterns of the protrusions in nonadjacent arrays of said adjacent anvil units are different.

8. The seam welder defined by claim 1, wherein
each of the patterns in which said protrusions are arranged comprises a plurality of regularly spaced protrusions, and
said patterns are differentiated from one another by omission of one or more different protrusions from each of said patterns.

9. The seam welder defined by claim 8, wherein each of said patterns comprises the protrusions each having a dimension of about 1 mm and being spaced from one another in both longitudinal and transverse directions of the nipper surface by about 0.5 to 2 mm.

10. The seam welder defined by claim 9, wherein each of said patterns comprises
columns of protrusions aligned in said longitudinal direction, and
rows of protrusions aligned in said transverse direction, wherein multiple protrusions are omitted from a central portion of said pattern.

11. A plurality of disposable wearing articles each comprising:
a pair of seam arrays comprising a plurality of intermittently arranged seam-welded regions, wherein
said seam arrays of different said disposable wearing articles include said seam-welded regions in a plurality of different patterns so that the disposable wearing articles are identifiable one from another,
in each of the seam arrays,
said seam-welded regions are arranged in a plurality of rows in a transverse direction of the seam array and a plurality of columns in a longitudinal direction of the seam array,
at least one of said seam-welded regions surrounded by (i) an outermost column and (ii) an outermost row is omitted, and
a location of the omitted seam-welded region varies from one of said disposable wearing articles to another.

12. The disposable wearing articles defined by claim 11, wherein said wearing articles, which have said seam arrays arranged in said different patterns and differentiated for every one of said wearing articles, are put in one package.

13. A plurality of disposable wearing articles each comprising:
a pair of seam arrays comprising a plurality of intermittently arranged seam-welded regions, wherein
said seam arrays of different said disposable wearing articles include said seam-welded regions in a plurality of different patterns so that the disposable wearing articles are identifiable one from another,
in each of the seam arrays, said seam-welded regions are arranged in a plurality of rows in a transverse direction of the seam array and a plurality of columns in a longitudinal direction of the seam array,
in each of the wearing articles, said seam arrays are aligned in the longitudinal direction thereof, and
the number of the seam-welded regions in a second row among the plurality of rows of said seam arrays varies from one of said seam arrays to another to define the plurality of different patterns of different said disposable wearing articles.

14. The disposable wearing articles defined by claim 13, wherein said wearing articles, which have said seam arrays arranged in said different patterns and differentiated for every one of said wearing articles, are put in one package.

15. The seam welder according to claim 1, wherein
in each of the nipper surfaces,
the protrusions are arranged in a plurality of rows in a transverse direction of the nipper surface and a plurality of columns in a longitudinal direction of the nipper surface,
at least one of said protrusions surrounded by (i) an outermost column and (ii) an outermost row is omitted, and
a location of the omitted protrusion varies from one of said nipper surfaces to another.

16. The seam welder according to claim 1, wherein
the protrusions include a plurality of rows in a transverse direction of the nipper surface, and
the number of the protrusions in one of the plurality of rows varies from one of said protrusions to another in each of said nipper surfaces.

\* \* \* \* \*